(12) United States Patent
Cuthbertson et al.

(10) Patent No.: US 7,368,474 B2
(45) Date of Patent: May 6, 2008

(54) RADIOFLUORINATION METHODS

(75) Inventors: Alan Cuthbertson, Nydalen (NO);
Magne Solbakken, Nydalen (NO);
Joseph Maduabuchi Arukwe, Nydalen (NO); Hege Karlsen, Nydalen (NO)

(73) Assignee: GE Healthcare Limited, Buckinghamshire (GB)

( * ) Notice: Subject to any disclaimer, the term of this patent is extended or adjusted under 35 U.S.C. 154(b) by 413 days.

(21) Appl. No.: 10/508,682

(22) PCT Filed: Mar. 20, 2003

(86) PCT No.: PCT/GB03/01332

§ 371 (c)(1),
(2), (4) Date: Sep. 20, 2004

(87) PCT Pub. No.: WO03/080544

PCT Pub. Date: Oct. 2, 2003

(65) Prior Publication Data

US 2005/0142061 A1 Jun. 30, 2005

(30) Foreign Application Priority Data

Mar. 22, 2002 (GB) ................................ 0206750.2

(51) Int. Cl.
*A61K 51/08* (2006.01)
*A61K 101/02* (2006.01)
(52) U.S. Cl. ..................... 514/453; 424/1.69; 424/1.89
(58) Field of Classification Search .................... None
See application file for complete search history.

(56) References Cited

U.S. PATENT DOCUMENTS 5,144,043 A 9/1992 Dean et al.

FOREIGN PATENT DOCUMENTS

EP 0203764 12/1986
EP 0289187 11/1988
WO 9911590 3/1999
WO 0177415 10/2001
WO 03006491 1/2003

OTHER PUBLICATIONS

Hwang, D.R., et.al., "Positron-Labeled Angiotensin-converting Enzyme (ACE) Inhibitor: Fluorine-18-Fluorocaptopril. Probing the Ace Activity in vivo by Positron Emission Tomography" Journal of Nuclear Medicine, Society of Nuclear Medicine, New York, US, vol. 32, No. 9 Sep. 1, 1991 pp. 1730-1737.
Okarvi, "Recent progress in fluorine-18 labelled peptide radiopharmaceuticals", Eur. J. Nuclear Medicine 2001, 28(7) pp. 929-938.
Int'l Search Report for PCT/GB03/01332 dated Jul. 23, 2003.
Great Britain Search Report for GB 0206750.2 dated Oct. 21, 2002.

*Primary Examiner*—Anish Gupta
*Assistant Examiner*—Ronald T Niebauer

(57) ABSTRACT

The present invention relates to methods and reagents for [$^{18}$F]-fluorination, particularly of peptides. The resultant $^{18}$F-labelled compounds are useful as radiopharmaceuticals, specifically for use in Positron Emission Tomography (PET). Thus, a compound of formula $^{18}$F-(Linker)-SH, such as a compound of formula (IV), (V), or (VI):

$$^{18}F\text{---}(CH_2CH_2O)_n\text{---}(CH_2)_m\text{---}SH \quad \text{(IV)}$$

$$^{18}F\text{---}(CH_2)_p\text{---}SH \quad \text{(V)}$$

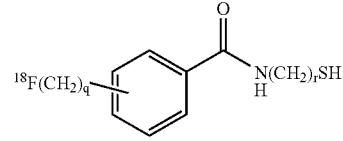

(VI)

may be reacted with an activated peptide as a means for $^{18}$F-labelling.

3 Claims, No Drawings

RADIOFLUORINATION METHODS

This application is a filing under 35 U.S.C. 371 of international application number PCT/GB03/01332, filed Mar. 20, 2003, which claims priority to application number 0206750.2 filed Mar. 22, 2002, in Great Britain the entire disclosure of which is hereby incorporated by reference.

FIELD OF INVENTION

The present invention relates to methods and reagents for [$^{18}$F]-fluorination, particularly of peptides. The resultant $^{18}$F-labelled compounds are useful as radiopharmaceuticals, specifically for use in Positron Emission Tomography (PET).

BACKGROUND OF THE INVENTION

The application of radiolabelled bioactive peptides for diagnostic imaging is gaining importance in nuclear medicine. Biologically active molecules which selectively interact with specific cell types are useful for the delivery of radioactivity to target tissues. For example, radiolabelled peptides have significant potential for the delivery of radionuclides to tumours, infarcts, and infected tissues for diagnostic imaging and radiotherapy. $^{18}$F, with its half-life of 110 minutes, is the positron-emitting nuclide of choice for many receptor imaging studies. Therefore, $^{18}$F-labelled bioactive peptides have great clinical potential because of their utility in PET to quantitatively detect and characterise a wide variety of diseases.

WO 99/11590 describes methods for [$^{18}$F]fluorination of thiol containing peptides and proteins.

One difficulty with $^{18}$F-labelled peptides is that the existing $^{18}$F-labelling agents are time-consuming to prepare. Efficient labelling of peptides and proteins with $^{18}$F is only achieved by using suitable prosthetic groups. Several such prosthetic groups have been proposed in the literature, including N-succinimidyl-4-[$^{18}$F]fluorobenzoate, m-maleimido-N-(p-[$^{18}$F]fluorobenzyl)-benzamide, N-(p-[$^{18}$F]fluorophenyl) maleimide, and 4-[$^{18}$F]fluorophenacylbromide. Almost all of the methodologies currently used today for the labelling of peptides and proteins with $^{18}$F utilise active esters of the fluorine labelled synthon. As peptides and proteins may contain a multitude of functional groups capable of reaction with active esters these current methods are not site-specific. For example a peptide containing 3 lysine residues has three amine functions all equally reactive towards the labelled synthon. Therefore, there still exists a need for $^{18}$F-labelled prosthetic groups and methodologies which allow rapid, chemoselective introduction of $^{18}$F, particularly into peptides, under mild conditions to give $^{18}$F-labelled products in high radiochemical yield and purity. Additionally, there is a need for such methodologies which are amenable to automation to facilitate preparation of radiopharmaceuticals in the clinical setting.

SUMMARY OF THE INVENTION

Accordingly, the present invention provides a method for radiofluorination comprising reaction of a compound of formula (I) or (Ia):

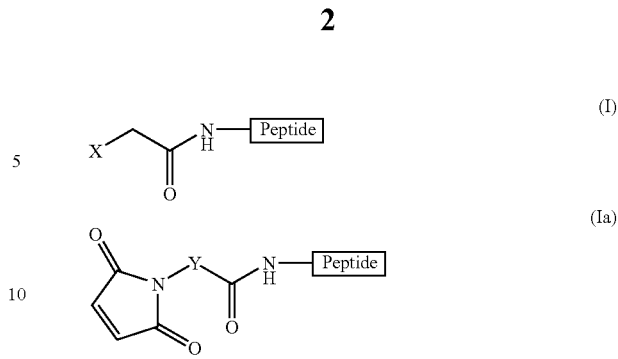

with a compound of formula (II):

wherein:
X is a leaving group selected from chloro, bromo, and iodo, and is preferably chloro;
Y is a $C_{1-10}$ hydrocarbyl group optionally including 1 to 6 heteroatoms; and
the Linker in formula (II) is a $C_{1-30}$ hydrocarbyl group optionally including 1 to 10 heteroatoms;
to give a compound of formula (III) or (IIIa) respectively:

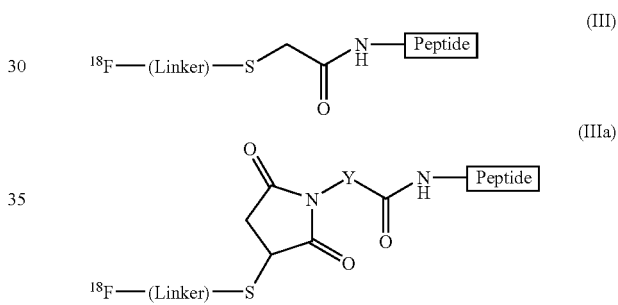

wherein the Linker group is as defined in the compound of formula (II), Y is as defined in the compound of formula (Ia), and the peptide is as defined in the compound of formula (I) or (Ia) respectively.

In a preferred aspect, the present invention provides a method for radiofluorination comprising reaction of a compound of formula (I):

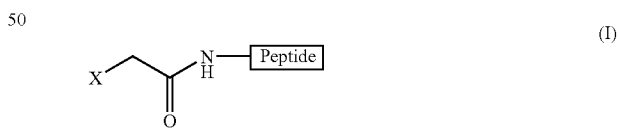

with a compound of formula (IV), (V), or (VI):

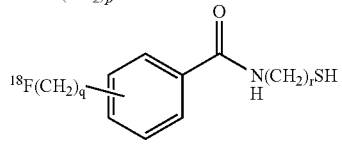

wherein:
X is a leaving group selected from chloro, bromo, and iodo, and is preferably chloro;
n is an integer of 1 to 20;
m is an integer of 1 to 10;
p is an integer of 1 to 20;
q is an integer of 0 to 4;
r is an integer of 1 to 10;
to give a compound of formula (VII), (VIII), or (IX) respectively:

(VII)

$^{18}F$—$(CH_2CH_2O)_n$—$(CH_2)_m$—S—CH$_2$—C(=O)—NH—[Peptide]

(VIII)

$^{18}F$—$(CH_2)_p$—S—CH$_2$—C(=O)—NH—[Peptide]

(IX)

$^{18}F(CH_2)_q$—C$_6$H$_4$—C(=O)—NH—$(CH_2)_r$—S—CH$_2$—C(=O)—NH—[Peptide]

wherein m, n, p, q, and r are as defined for the compound of formula (IV), (V), or (VI).

In a further preferred aspect, the present invention provides a method for radiofluorination comprising reaction of a compound of formula (Ia):

(Ia)

[maleimide]-N-Y-C(=O)-NH-[Peptide]

with a compound of formula (IV), (V), or (VI):

$^{18}F$—$(CH_2CH_2O)_n$—$(CH_2)_m$—SH    (IV)

$^{18}F$—$(CH_2)_p$—SH    (V)

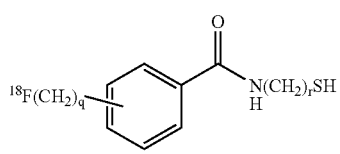    (VI)

wherein:
Y is a $C_{1-10}$ hydrocarbyl group optionally including 1 to 6 heteroatoms;
n is an integer of 1 to 20;
m is an integer of 1 to 10;
p is an integer of 1 to 20;
q is an integer of 0 to 4;
r is an integer of 1 to 10;
to give a compound of formula (X), (XI), or (XII) respectively:

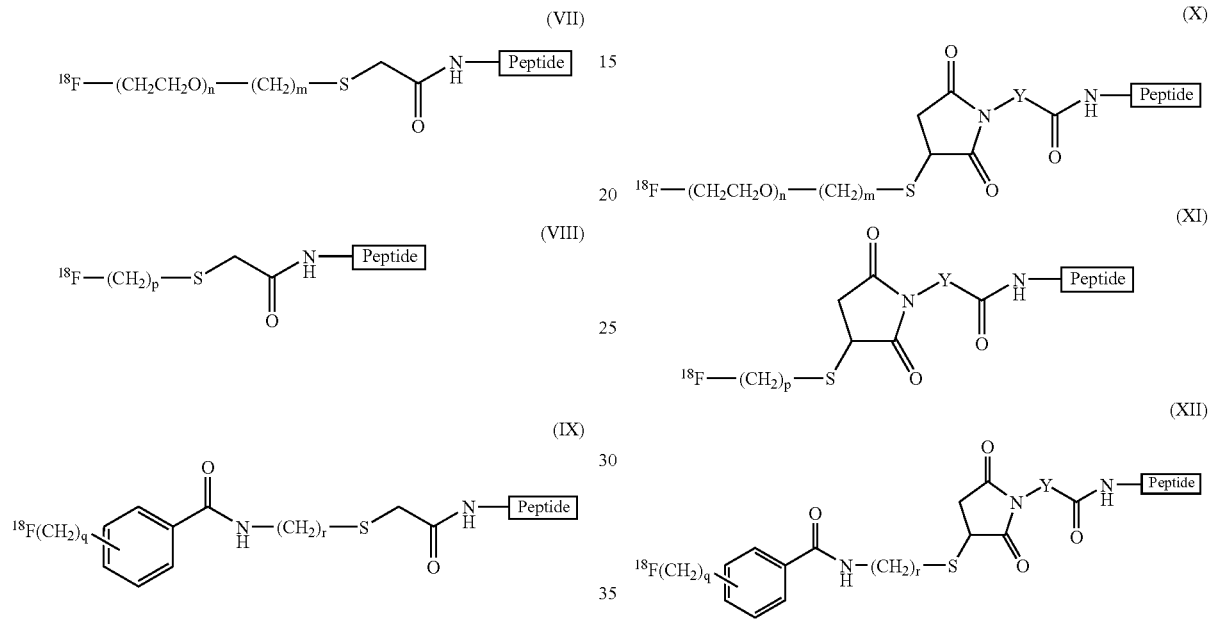

wherein m, n, p, q, and r are as defined for the compound of formula (IV), (V), or (VI), Y and the peptide are defined for the compound of formula (Ia).

As a further aspect of the invention, there is provided a compound of formula (IV), (V), or (VI) as defined above.

As a further aspect of the invention, there is provided a compound of formula (VII), (VIII), (IX), (X), (XI), or (XII) as defined above. These compounds having utility as PET tracers.

DETAILED DESCRIPTION OF THE PREFERRED EMBODIMENTS OF THE INVENTION

This reaction may be effected in a suitable solvent, for example, in an aqueous buffer in the pH range 5 to 11, and at a non-extreme temperature of from 5 to 60° C., preferably at ambient temperature.

In formula (I) and (Ia), suitable peptides for labelling may include somatostatin analogues, such as octreotide, bombesin, vasoactive intestinal peptide, chemotactic peptide analogues, α-melanocyte stimulating hormone, neurotensin, Arg-Gly-Asp peptide and its analogues, human pro-insulin connecting peptide, endothelin, angiotensin and formyl-norleucyl-leucyl-phenylalanyl-norleucyl-tyrosyl-lysine.

Preferred peptides for labelling are Arg-Gly-Asp peptide and its analogues, such as those described in WO 01/77415 and WO 03/006491. In one particular aspect, the peptide in formula (I) or (Ia) is of formula (A):

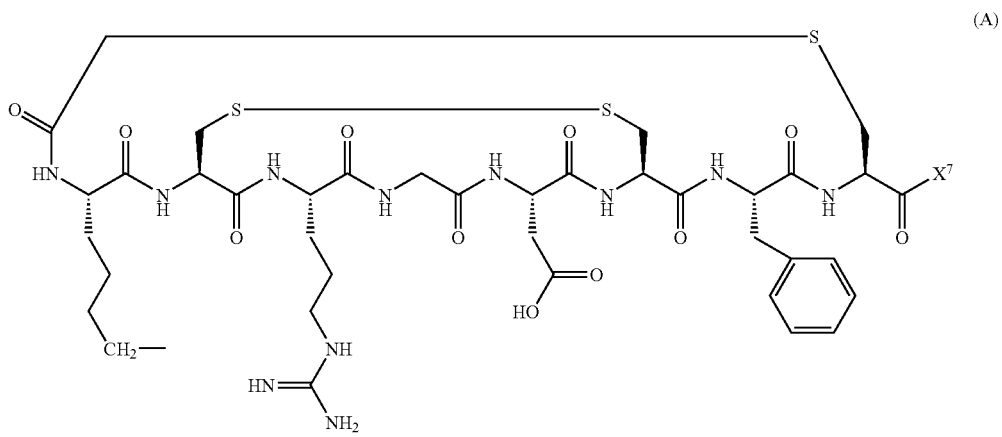

(A)

wherein X⁷ is either —NH₂ or

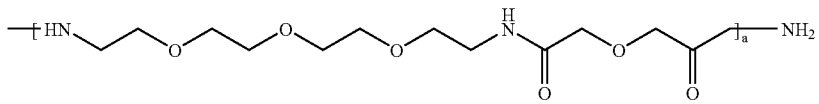

wherein a is an integer of from 1 to 10, preferably a is 1.

As will be appreciated by the skilled person, the methods of the invention may also be used for radiofluorination of other biomolecules such as proteins, hormones, oligonucleotides, and antibody fragments, as well as small molecules to provide a variety of PET tracers.

In formula (Ia), Y is a $C_{1-10}$ hydrocarbyl group optionally including 1 to 6 heteroatoms such as oxygen or nitrogen, suitably Y is a $C_{1-10}$ alkyl group optionally including a $C_{4-7}$cycloalkyl group, for example Y may be methylcyclohexyl.

In formula (II) the Linker is a $C_{1-30}$ hydrocarbyl group optionally including 1 to 10 heteroatoms such as oxygen or nitrogen, and may be chosen to provide good in vivo pharmacokinetics, such as favourable excretion characteristics. Suitable Linker groups include alkyl, alkenyl, alkynyl chains, aromatic, polyaromatic, and heteroaromatic rings, and polymers comprising ethyleneglycol, amino acid, or carbohydrate subunits.

In the compounds of formulae (IV) and (VII), n is typically 2 to 6, suitably 3, and m is typically 1 to 4, suitably 2.

In the compounds of formulae (V) and (VIII), p is typically 1 to 6, suitably 3.

In the compounds of formulae (VI) and (IX), the group $^{18}F(CH_2)_q$— is suitably attached in the para position relative to the amide group, q is typically 0 to 4, suitably 1, and r is typically 1 to 4, suitably 2.

As a further aspect of the invention, there is provided a compound of formula (IV), (V), or (VI) as defined above. These compounds having general utility as prosthetic groups for radio-fluorination. Thiol protected derivatives of the compounds of formulae (IV), (V), and (VI) also have utility as synthetic precursors for such prosthetic groups, and those wherein the thiol is protected by a trityl group are particularly preferred. Other thiol protecting groups in precursors of formula (IV), (V), or (VI) are well known to the person skilled in the art and are described, for example, in Protecting Groups in Organic Synthesis, Theodora W. Greene and Peter G. M. Wuts, published by John Wiley & Sons Inc.

As a further aspect of the invention, there is provided a compound of formula (VII), (VIII), (IX), (X), (XI), or (XII) as defined above. These compounds having utility as PET tracers. Of these compounds, those in which the peptide is Arg-Gly-Asp peptide or its analogues are preferred, such as the peptides described in WO 01/77145 and WO 03/006491. Particularly preferred peptides in this aspect of the invention are those of formula (A) as defined above for the compounds of formula (I) and (Ia).

Compounds of formula (I) may be prepared by standard methods of peptide synthesis, for example, solid-phase peptide synthesis, for example, as described in Atherton, E. and Sheppard, R. C.; "Solid Phase Synthesis"; IRL Press: Oxford, 1989. Incorporation of the group "X—CH₂C(O)—" in a compound of formula (I) may be achieved by reaction of the N-terminus of the peptide with the reagent of formula (XIII):

$$X-CH_2C(O)Z \quad (XIII)$$

under standard conditions for peptide bond formation; wherein X is as defined for the compound of formula (I), and Z is —OH or a suitable activating group such as, chloro, bromo, fluoro, —OC(O)CH₂—X wherein X is as defined for the compound of formula (I), or when Z is —OH the acid may be activated using in situ agents such as 2-(1H-benzotriazole-1-yl)-1,1,3,3-tetramethyluronium hexafluorophosphate (HBTU) or N-[(dimethylamino)-1H-1,2,3-triazolo[4,5-b]pyridin-1-ylmethylene]-N-methylmethanaminium hexafluorophosphate N-oxide (HATU).

Compounds of formula (Ia) may be prepared by standard methods of peptide synthesis, for example, solid-phase peptide synthesis, for example, as described in Atherton, E. and Sheppard, R. C.; "Solid Phase Synthesis"; IRL Press:

Oxford, 1989. Incorporation of the group maleimide-Y—" in a compound of formula (Ia) may be achieved by reaction of the N-terminus of the peptide with the reagent of formula (XIV):

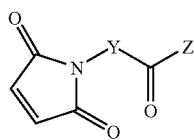

(XIV)

under standard conditions for peptide bond formation; wherein Y is as defined for the compound of formula (Ia), and Z is —OH or a suitable activating group such as, chloro, bromo, fluoro, or active esters such as pentafluorophenol or N-hydroxysuccinimide ester, or when Z is —OH then the acid may be activated by use of in situ activating agents such as HBTU or HATU as described above for the compound of formula (XIII).

Compounds of formula (II) may be prepared from the corresponding compound of formula (IIa):

L-(Linker)-SR       (IIa)

wherein L is a leaving group such as p-toluenesulphonate, trifluoromethanesulphonate, or methanesulphonate, and the Linker is as defined for the compound of formula (II) and R is hydrogen or a thiol protecting group; by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at elevated temperature, for example 60 to 120° C., followed by removal of any thiol protecting group using standard methods.

Compounds of formula (IV) may be prepared from the corresponding compound of formula (IVa):

L-($CH_2CH_2O$)$_n$—($CH_2$)$_m$—SR       (IVa)

wherein L is a leaving group such as p-toluenesulphonate, trifluoromethanesulphonate, or methanesulphonate, and n and m are as defined for the compound of formula (IV) and R is hydrogen or a thiol protecting group; by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at elevated temperature, for example 60 to 120° C., followed by removal of any thiol protecting group using standard methods.

Compounds of formula (V) may be prepared from the corresponding compound of formula (Va):

L-($CH_2$)$_p$—SR       (Va)

wherein L is a leaving group such as p-toluenesulphonate, trifluoromethanesulphonate, or methanesulphonate, and p is as defined for the compound of formula (V) and R is hydrogen or a thiol protecting group; by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at elevated temperature, for example 60 to 120° C., followed by removal of any thiol protecting group using standard methods.

Compounds of formula (VI) may be prepared from the corresponding compound of formula (VIa):

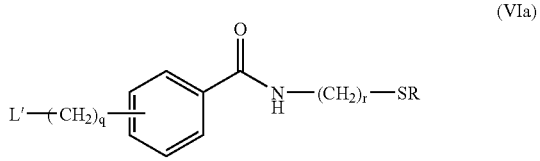

(VIa)

wherein L' is a leaving group such as iodo, p-toluenesulphonate, trifluoromethanesulphonate, or methanesulphonate and when q is 0, L' can be nitro or an iodonium or ammonium salt, and q and r are as defined for the compound of formula (VI) and R is hydrogen or a thiol protecting group; by reaction with cyclotron produced aqueous [$^{18}$F]-fluoride, suitably pre-activated by evaporation from a base (for example, from tetrabutylammonium or $K_2CO_3$/Kryptofix-222), in a suitable solvent such as acetonitrile, N,N-dimethylformamide, or dimethyl sulphoxide, typically at elevated temperature, for example 60 to 120° C., followed by removal of any thiol protecting group using standard methods.

In formulae (IIa), (IVa), (Va), and (VIa), suitable thiol protecting groups include (Phenyl)$_3$C-(trityl) and others as may be found described in Protecting Groups in Organic Synthesis, Theodora W. Greene and Peter G. M. Wuts, published by John Wiley & Sons Inc. Removal of such thiol protecting groups may be effected by standard methods, such as those described in Greene. For example, where R is trityl, the free thiol may be formed by treatment with dilute acid, for example trifluoroacetic acid in a chlorinated solvent, such as dichloromethane.

In one preferred aspect, the compounds of formulae (IIa), (IVa), (Va), and (VIa) may be bound to a solid support, such as polymer beads or coatings, for example, a trityl or chlorotrityl resin. In this aspect, the excess reagents and by-products of the radio-fluorination reaction may be separated from the polymer-bound product by washing. Using the deprotection methods as described above, effects cleavage of the compound of formula (II), (IV), (V), or (VI) from the solid support. This approach may be particularly suitable for automated production of the compounds of formulae (II), (IV), (V), and (VI). Alternatively, the by-products of thiol deprotection, where insoluble in the reaction mixture, may be removed by filtration.

According to a further aspect of the invention there is provided a kit for the preparation of a radiofluorinated tracer comprising a prosthetic group of formula (IIa), (IVa), (Va), or (VIa) and an activated peptide of formula (I) or (Ia).

In use of the kit, the compound of formula (IIa), (IVa), (Va), or (VIa) would be converted to the corresponding compound of formula (II), (IV), (V), or (VI) using methods described above. Preferably, the compound of formula (II), (IV), (V), (VI) or a thiol protected precursor of any thereof, may be separated from waste reactants by passing the reaction mixture through a Solid Phase Extraction (SPE) cartridge. The SPE cartridge may comprise a graphite pad or $C_{18}$ stationary phase. Any thiol protecting group may be removed, for example, by addition of an acid such as trifluoroacetic acid. Where the thiol group in the compound of formula (II), (IV), (V), or (VI) is protected with a hydrophobic group, such as a trityl group, the deprotection may conveniently be effected on the SPE cartridge, whereby the hydrophobic thiol protecting group (such as trityl) remains bound on the stationary phase while the labelled prosthetic group of formula (II), (IV), (V), or (VI) is eluted in high purity and yield. The compound of formula (II), (IV), (V), or (VI) would then be added to the compound of formula (I) or (Ia) which may suitably be dissolved in aqueous buffer (pH 7-11). After reaction at a non-extreme temperature for 1 to 60 minutes, the labelled peptide may be purified, for example, by SPE and collected.

The invention is illustrated by way of the following examples.

EXAMPLES

Production of $^{18}F$

Fluorine-18 was produced by a cyclotron using the $^{18}O$ (p,n)$^{18}F$ reaction. Enriched [$^{18}O$]H$_2$O(95% $^{18}O$) was irradiated by protons (19 MeV) with an integrated beam current of 5-10 μAh.

Synthesis of ClCH$_2$CO-Lys-Gly-Phe-Gly-Lys-OH peptide

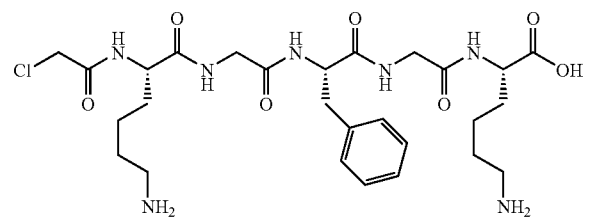

Assembly of the amino acid sequence using fully automated synthesis (ABI 433A), Lys-sasrin resin (0.10 mmol) and 10 mmol cartridges of aminoacids. After the peptide synthesis the peptide on resin was placed in a manual bubbler apparatus and washed with N,N dimethylformamide (DMF) and freshly made chloroacetic anhydride (0.5 mmol) (chloroacetic acid (94.5 mg, 1.0 mmol) and dicyclohexyl-carbodiimide (DCCl) (102.6 mg, 0.5 mmol) in dichloromethane (DCM) for 10 minutes. Dicyclohexylurea (DCU) filtered off and the solution was evaporated under reduced pressure affording the anhydride) in DMF was added. After 1 hour the Kaiser test was negative (yellow, red resin (due to the anhydride)), the solvent removed, and the resin washed with DMF 8 times then DCM and diethyl ether (DEE) and N$_2$-dried. triisopropylsilane (TIS) and a drop of;water were added to the resin before trifluoroacetic acid (TFA) was added. The resin was filtered off after 50 minutes and the solution evaporated under reduced pressure and washed with DEE 3 times. The crude product was purified by reverse phase preparative chromatography affording 64.3 mg of pure product (Vydac 218TP1022 column; solvents A=water/0.1% TFA and B=CH$_3$CN/0.1% TFA; gradient 00-30% B over 40 min; flow 10 ml/minute; detection at 254 nm). (Analytical HPLC: Phenomenex Luna 00B-4251-E0 column; solvents: A=water/0.1% TFA and B=CH$_3$CN/0.1% TFA; gradient 00-30% B over 10 min; flow 2.0 ml/minute; retention time 5.1 minutes detected at 214 and 254 nm).Further characterisation was carried out using mass spectrometry, giving m/z value 612.8[MH$^+$].

Example 1

Preparation of 4-Fluoromethyl-N-[2-(tritylsulpha-nyl)ethyl]benzamide, Deprotection and Site-specific Conjugation to a Chloroacetyl Modified Peptide 1. a) S-Trityl Cysteamine

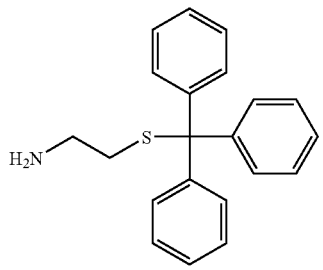

To a stirred solution of cysteamine (Fluka, 3.85 g, 50.0 mmol) in trifluoroacetic acid (TFA) (50 ml) was added triphenylmethanol (13.0 g, 50.0 mmol). The mixture was stirred at room temperature for 30 min and concentrated. To the residue was added ether (250 ml). Precipitated material was filtered off and washed with ether. The TFA-salt was partitioned between 1 M aqueous KOH solution (150 ml) and ether (150 ml). The phases were separated and the ether phase was dried (MgSO$_4$). The solution was filtered and concentrated and the product was crystallised from ether/n-hexane, giving 9.20 g (58%) of white solid.

1. b) 4-Hydroxymethyl-N-[2-(tritylsulphanyl)ethyl]benzamide

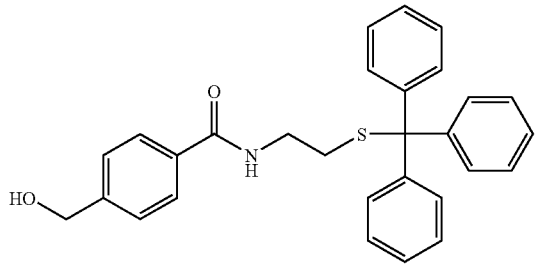

To a solution of S-trityl cysteamine (1.60 g, 5.00 mmol) and 4-hydroxymethylbenzoic acid pentafluorophenyl ester (MilliGen, 1.51 g, 5.00 mmol) in dichloromethane (40 ml) was added N-methylmorpholine (0.55 ml, 5.0 mmol). The mixture was stirred at room temperature for 36 hrs. Precipitated material was filtered off, washed with dichloromethane and dried to give 1.30 g (57%) of white solid. NMR analysis was in accordance with the structure.

1. c) Methanesulphonic acid 4-[2-(tritylsulphanyl)ethylcar-bamoyl]benzyl ester

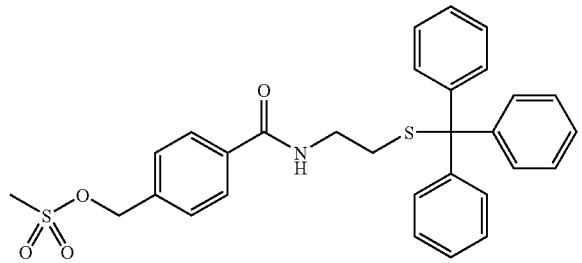

To a solution of 4-hydroxymethyl)-N-[2-(tritylsulphanyl)ethyl]benzamide (226 mg, 0.500 mmol) in dry THF (8 ml) was added N-methyl pyrrolidinone (NMP) (61 μl, 0.55 mmol) and mesyl chloride (85 μl, 1.1 mmol). The reaction mixture was stirred at room temperature for 48 hours, filtered through silica and concentrated. The product was purified by column chromatography (silica, 1% methanol in chloroform) to give 213 mg of an oil that solidified slowly. NMR analysis was in accordance with the structure.

1. d) 4-Fluoromethyl-N-[2-(tritylsulphanyl)ethyl]benzamide

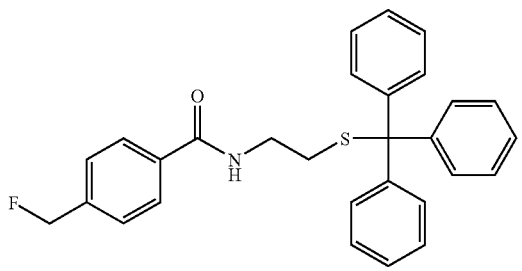

A solution of Kryptofix (Fluka, 15 mg, 40 μmol) in dry acetonitrile (200 μl) was added to solid potassium fluoride (2.3 mg, 80 μmol). The mixture was shaken for 5 min. The Kryptofix/KF-solution was added to a solution of methane-sulphonic acid 4-[2-(tritylsulphanyl)ethylcarbamoyl]benzyl ester (21 mg, 40 μmol) in acetonitrile (400 μl). The mixture was heated at 65° C. for 10 min. An aliquot was analysed by HPLC (column Phenomenex Luna 3 μm C18(2) 50×4.60 mm; solvents: A=water/0.1% TFA and B=acetonitrile/0.1% TWA; gradient 40-80% B over 10 min; flow 2.0 ml/min, UV detection at 214 and 254 nm), showing complete conversion of starting material ($t_R$ 5.6 min) to a new product ($t_R$ 6.3 min). Purification by reverse phase preparative HPLC (column: Phenomenex Luna C18(2) 5 μm 250×21.2 mm, solvents: A=water/0.1% TFA and B=acetonitrile/0.1% TFA; gradient 40-80% B over 60 min; flow 10.0 ml/min, UV detection at 214 nm) gave 4.5 mg of white solid. The structure was confirmed by NMR spectroscopy.

1. e) 4-Fluoromethyl-N-(2-mercaptoethyl)benzamide

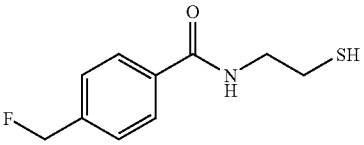

To 1.4 mg (3.0 μmol) of 4-fluoromethyl-N-[2-(tritylsulphanyl)ethyl]benzamide was added 50 μl of TFA/TIS/H$_2$O (95:2.5:2.5) mixture. The flask was swirled gently for 5 minutes and then concentrated in vacuo. LC-MS analysis (column Phenomenex Luna 3 μm C18(2) 50×2.00 mm; solvents: A=water/0.1% HCOOH and B=acetonitrile/0.1% HCOOH; gradient 5-60% B over 10 min; flow 0.3 ml/min, UV detection at 214 and 254 nm, ESI-MS) gave a peak ($t_R$ 6.8 min) with m/z at 214 corresponding to MH$^+$.

1. f) Site-specific Conjugation to the Chloroacetyl Modified Peptide

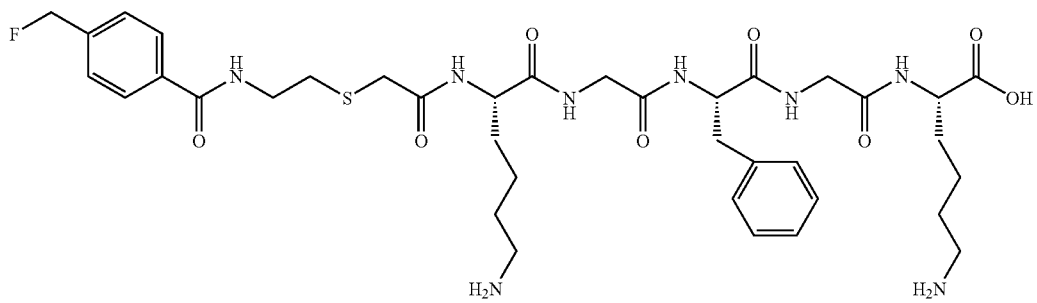

The residue from above was taken up in 100 μl 0.1 M sodium hydrogencarbonate/disodium carbonate buffer at pH 9.1. To the mixture was added a solution of the peptide chloroacetyl-KGFGK—OH (3.7 mg, 6.0 μmol) in 150 μl buffer. The mixture was heated at 45° C. for 20 min. LC-MS analysis (column Phenomenex Luna 3 μm C18(2) 50×2.00 mm; solvents: A=water/0.1% HCOOH and B=acetonitrile/0.1% HCOOH; gradient 5-60% B over 10 min; flow 0.3 ml/min, UV detection at 214 and 254 nm, ESI-MS) showed complete conversion of the fluoro compound to a new product($t_R$ 4.3 min) giving m/z at 789.4 corresponding to MH+ for the conjugate. The conjugate product was purified by reverse phase HPLC (column: Phenomenex Luna C18(2) 5 μm 250×21.2 mm, solvents: A=water/0.1% TFA and B=acetonitrile/0.1% TFA; gradient 5-60% B over 60 min; flow 10.0 ml/min, UV detection at 214 nm) to give 2 mg of white solid.

Example 2

Preparation of (3-fluoro-propylsulfanyl)triphenylmethane, Deprotection and Site-specific Conjugation to a Chloroacetyl Peptide 2. a) Synthesis of 3-tritylsulfanyl-propan-1-ol

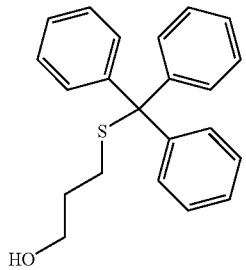

Trityl chloride (27.9 mg, 0.1 mmol) and triethyl amine (49 μl, 0.5 mmol) were dissolved in DCM (2 ml) before 3-mercapto-1-propanol (9 μl, 0.1 mmol) was added. DCM was evaporated under reduced pressure after 6 hours and the crude product purified by reverse phase preparative chromatography (Vydac 218TP1022 column; solvents A=water/0.1% TFA and B=CH₃CN/0.1% TFA; gradient 30-70 % B over 40 min; flow 10 ml/minute; detection at 254 nm). A yield of 6 mg of purified material was obtained (analytical HPLC: column phenomenex Luna C18,00B-4251-E0: solvents: A=water/0.1% TFA and B=CH₃CN/0.1% TFA; gradient 30-70% B over 10 min; flow 1.0 ml/minute; retention time 7.73 minutes detected at 214 and 254 nm). Structure verified by NMR.

2. b) Synthesis of methanesulfonic acid 3-tritylsulfanyl-propyl ester

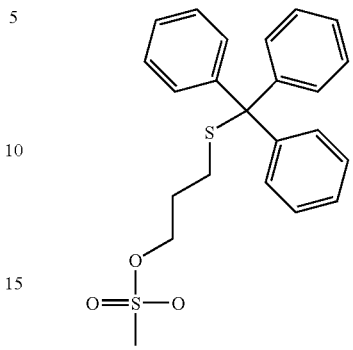

Mesyl chloride (6 μl, 0.075 mmol) was added to a solution of 3-tritylsulfanyl-propan-1-ol (5 mg, 0.015 mmol) and triethyl amine,(32 μl, 0.23 mmol) in THF (1 ml). After 30 minutes THF was evaporated under reduced pressure and the crude product dissolved in DCM, washed with a saturated solution of sodium hydrogencarbonate in water, a saturated solution of sodium chloride and dried with MgSO₄. A yield of 10 mg was obtained after evaporation under reduced pressure (analytical HPLC: column Luna C18, 00B-4251-E0: solvents: A=water/0.1% TFA and B=CH₃CN/0.1% TFA; gradient 40-80% B over 10 min; flow 1.0 ml/minute; retention time 7.12 minutes detected at 214 and 254 nm). Structure verified by NMR.

2. c) Synthesis of (3-fluoro-propylsulfanyl)triphenylmethane

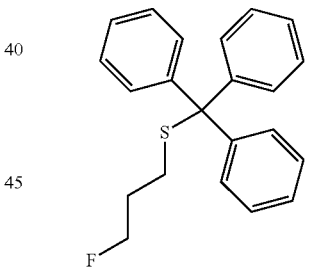

KF (1.4 mg, 0.024 mmol) and Kryptofix 222 (9.0 mg, 0.024 mmol) were dissolved in acetonitrile (0.2 ml) (heating). Methanesulfonic acid 3-tritylsulfanyl-propyl ester (5 mg, 0.012 mmol) in acetonitrile (0.2 ml) was added. The reaction mixture was heated to 80 degrees for 90 minutes. The crude product was purified by reverse phase preparative chromatography (Vydac 218TP1022 column; solvents A=water/0.1% TFA and B=CH₃CN/0.1% TFA; gradient 40-90% B over 40 min; flow 10 ml/minute; detection at 254 nm). A yield of 2 mg of purified material was obtained (analytical HPLC: column Phenomenex Luna C18, 00B4251-E1: solvents: A=water/0.1% TFA and B=CH₃CN/0.1% TFA; gradient 40-80% B over 10 min; flow 1.0 ml l/minute; retention time 8.2 minutes detected at 214 and 254 nm). Structure verified by NMR.

2. d) Conjugation of 3-fluoro-propane-1-thiol with Cl—Ac-Lys-Gly-Phe-Gly-Lys-OH

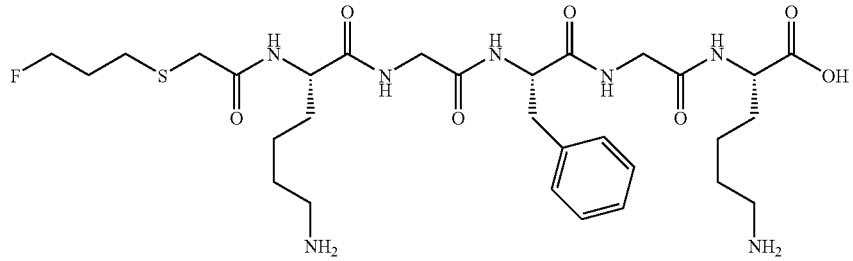

The trityl group from (3-fluoro-propylsulfanyl)triphenyl-methane (1.0 mg, 0.003 mmol) was cleaved with TFA (25 µl) in the presence of TIS (5 11) and water (5 µl) (5 minutes). The TFA solution was cooled on ice during addition of ammonia (25%) until pH was 9. A solution of $ClCH_2CO$—KGFGK—OH 3.6 mg, 0.006 mmol) in 50 µl of water was added and the pH adjusted to 9 with ammonia. The reaction mixture was heated to 60 degrees for 30 minutes. The reaction mixture was quenched with water +0.1% TFA and purified using reverse phase preparative chromatography (Phenomenex, C18, 00G-4253-NO column; solvents A=water/0.1% TFA and B=$CH_3CN$/0.1% TFA; gradient 00-30% B over 30 min; flow 5 ml/minute; detection at 254 nm). A yield of 0.4 mg of purified material was obtained (analytical HPLC: column Luna 00B4251-E0: solvents: A=water/0.1% TFA and B=$CH_3CN$/0.1% TFA; gradient 00-30% B over 10 min; flow 1.0 ml/minute; retention time 6.88 minutes detected at 214 and 254 nm). Further characterisation was carried out using mass spectrometry, giving m/z value 670.35. [M-H$^+$].

Example 3

Preparation of (2-{2-[2-(2-Fluoro-ethoxy)-ethoxy]-ethoxy}-ethyl)-trityl sulfide, Deprotedtion and Site-specific Conjugation to a Chloroacetyl Modified Peptide 3. a) Toluene-4-Sulfonic acid 2-{2-[2-(2-hydroxy-ethoxy]-ethoxy}-ethoxy-ethyl ester

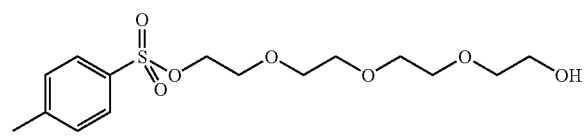

To a stirred suspension of p-toluenesulfonyl chloride (9.82 g, 51.5 mmol) in 2-{2-[2-(2-hydroxy-ethoxy)-ethoxy]-ethoxy}-ethanol, (20 g, 103 mmol) at 0° C. was added dropwise triethylamine (13 ml, 93 mmol). The suspension was stirred at 0° C. for 1 hour and then at room temperature for another 16 hours. The resulting mixture was dissolved in dichloromethane (350 ml). The clear and colourless solution that was obtained was extracted with 1 M hydrochloric acid (2×100 ml) and once with water (200 ml). The organic phase was dried (MgSO$_4$), filtered and evaporated to afford a colourless oil. The crude product was purified by flash chromatography using ethyl acetate. Tetraethylene glycol ditosylate, eluted first followed by toluene-4Sulfonic acid 2-{2-[2-(2-hydroxy-ethoxy)ethoxy]-ethoxy}-ethyl ester, as a colourless oil; 8.89 g (49%).

3. b)2-{2-[2-(2-Mercapto-ethoxy)-ethoxy]-ethoxy}-ethanol

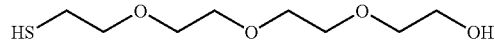

A solution of thiourea (0.94 g, 12.35 mmol) and toluene-4-sulfonic acid 2-{2-[2-(2-hydroxy-ethoxy)-ethoxy]-ethoxy)-ethyl ester (4.09 g, 11.75 mmol) in absolute alcohol (32 ml) was heated to reflux under argon atmosphere for 24 h. The mixture was cooled and a solution of NaOH (1.23 g, 30.75 mmol) in 15 ml of ethanol/water (9:1, v/v) was added. Refluxing was continued for another 2.5 h under argon. The reaction mixture was then cooled to ambient temperature and acidified to pH 2 using concentrated hydrochloric acid and then concentrated under reduced pressure. The residue was purified by flash chromatography using ethyl acetate/absolute ethanol (10:1) to afford the product as a colourless oil. Yield 1.55 g (66%).

3. c) 2-{2-[2-(2-Tritylsulfanyl-ethoxy)-ethoxy]-ethoxy}-ethanol

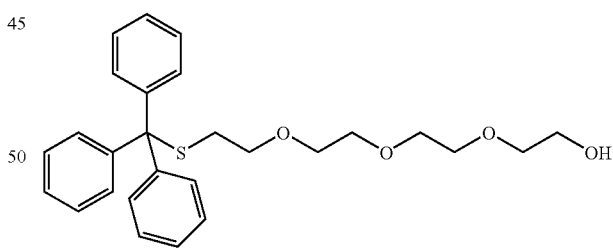

To 2-{2-[2-(2-mercapto-ethoxy)-ethoxy]-ethoxy}-ethanol (310 mg, 1.47 mmol) and trityl chloride (452 mg, 1.62 mmol, 1.1 eq.) in a round bottomed flask was added simultaneously triethylamine (2.1 ml, 10 eq.) and THF (25 ml) under argon. The initial red colour faded upon stirring at ambient temperature for 1 hour. The reaction was monitored by TLC, ethyl acetate/ethanol (1:1) and was completed after 6 hours. Thereafter methanol (6 ml) was added to consume excess trityl chloride and the mixture stirred for 5 minutes before evaporation of the solvents. The residue was purified by flash chromatography using 100% ethyl acetate to afford the product (550 mg, 83%) as a colourless oil.

3 d) Methanesulfonic acid 2-{2-[2-(2-tritylsulfanyl-ethoxy)-ethoxy]-ethoxy}ethyl ester

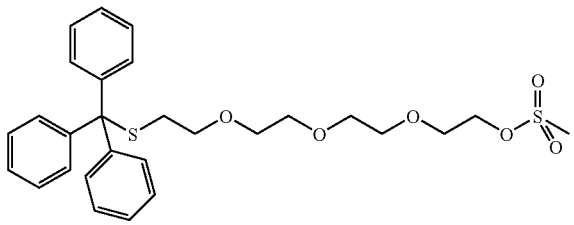

To a stirring THF (12 ml) solution of 2-{2-[2-(2-Tritylsulfanyl-ethoxy)-ethoxy]-ethoxy}-ethanol (227 mg, 0.50 mmol) and triethylamine (139 µl, 1.0 mmol) was added methyl sulfonyl chloride (47 µl, 0.60 mmol, 1.2 eq.). After stirring for 2 hours at ambient temperature, the mixture was filtered to eliminate precipitated triethylamine hydrochloride salt and the solvents were evaporated. The residue was purified by flash chromatography to afford the product (238 mg, 90%) as a colourless oil.

3. e) Synthesis of (2-{2-[2-(2-Fluoro-ethoxy)-ethoxy]-ethoxy}ethyl)-trityl sulfide

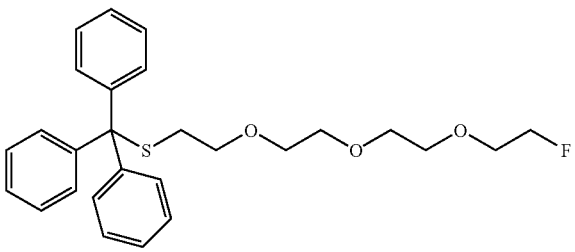

A stirring solution of methanesulfonic acid 2-{2-[2-(2-tritylsulfanyl-ethoxy)-ethoxy]-ethoxy}-ethyl ester (71.67 mg, 0.14 mmol) and tetrabutylammonium fluoride (1.1 M in THF, 127 µl, 0.14 mmol) was heated at 90° C. for 30 minutes. The mixture was cooled to ambient temperature and evaporated to dryness. Purification of product was by flash chromatography using ethyl acetate/hexane, (1:1) to give the product (71%) as a colourless oil.

Example 3. f)

Deprotection of the Trityl Group and Site-specific Conjugation to the Chloroacetyl Peptide Deprotection of the trityl group and site-specific conjugation to the chloroacetyl functionalised peptide was carried out as described, in example 1. e) and f) above.

HPLC Method for Examples 4 to 6

Beckman System Gold®, column: Luna (Phenomenex), C18, 3 µm, 50×4.6 mm i.d.; flow rate 1 ml/min; solvent A: water (0.1%) TFA, solvent B: acetonitrile (0.1% TFA).

gradient system 1: 1 min 40% B, 15 min 40→80% B, 5 min 80% B gradient system 2: 1 min 0% B, 10 min 0→30% B, 5 min 30% B, 5 min 30→80% B Example 4

Preparation of 4-[$^{18}$E]-Fluoromethyl-N-[2-(tritylsulphanyl)ethyl]-benzamide, Deprotection and Site-specific Conjugation to a Chloroacetyl Modified Peptide 4.a) Preparation of 3-[$^{18}$F]Fluoromethyl-N-(2-mercaptotrityl-ethyl)-benzamide

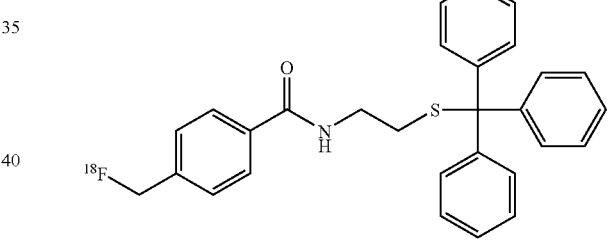

The preparation was carried out by methods analogous to those described in example 5 a). The mesylate precursor prepared as described in Example 1 c) was stirred at room temperature for 15 minutes to give desired product in a 22% radiochemical yield (HPLC).

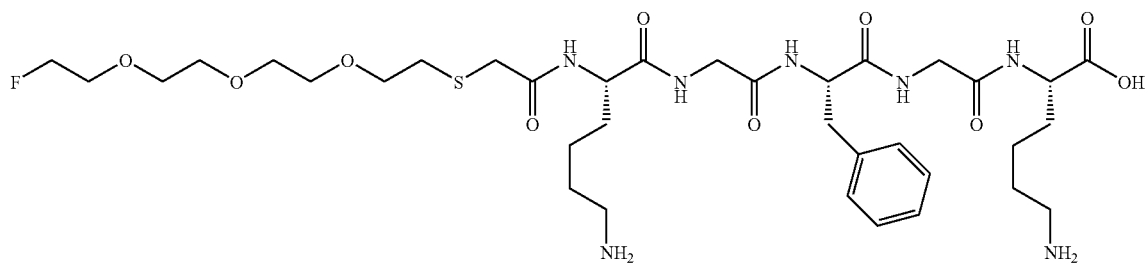

4.b) Chemoselective ligation to peptide Cl—CH₂CO-Lys-Gly-Phe-Gly-Lys-OH

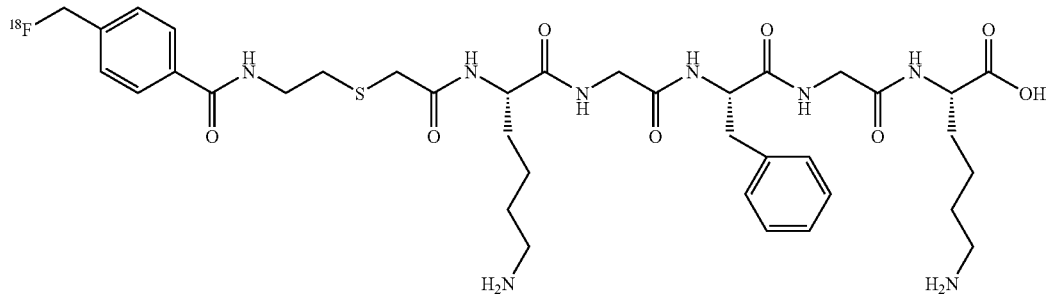

The deprotection and ligation of $^{18}$F-synthon from Example 4a) with peptide precursor Cl—CH₂CO-Lys-Gly-Phe-Gly-Lys-OH was carried out following the methods described in example 5. HPLC analysis revealed formation of the desired product with a radiochemical purity of 80%.

Example 5

Preparation of (3-[$^{18}$F]-fluoro-propylsulfanyl)triphenylmethane, Deprotection and Site-specific Conjugation to a Chloroacetyl Peptide 5.a) Preparation of $^{18}$F synthon: 3-f[$^{18}$F]fluoro-1-mercaptotrityl-propane

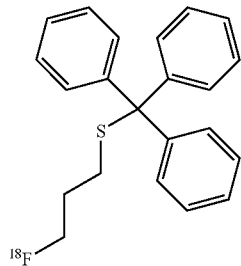

To a Wheaton vial (2 ml) charged with Kryptofix® 222 (10 mg), potassium carbonate (1 mg dissolved in 50 μl water), and acetonitrile (0.8 ml) the fluorine-18 containing water (10 mCi, 1 ml) was added. The solvent was removed by heating at 110° C. for one hour under a stream of nitrogen. Anhydrous acetonitrile (0.5 ml) was added and again evaporated as before. This step was repeated twice. The vial was cooled to room temperature followed by injecting a solution of mesylate prepared as described in Example 2 b) (1 mg) in anhydrous DMSO (0.2 ml). The reaction mixture was stirred at 80° C. for 5 min and analysed by HPLC (gradient 1, radiochemical yield 90%).

The reaction mixture was diluted with DMSO/water (1:1 v/v, 0.15 ml) and loaded onto a SepPak-Plus cartridge (ᵗC18, Waters) that had been conditioned (10 ml acetonitrile, 20 ml water). The cartridge was washed with water (10 ml) and the product eluted using acetonitrile. The radiochemical purity was 99%.

5.b) Chemoselective ligation of a) to Cl—CH₂CO-Lys-Gly-Phe-Gly-Lys-OH

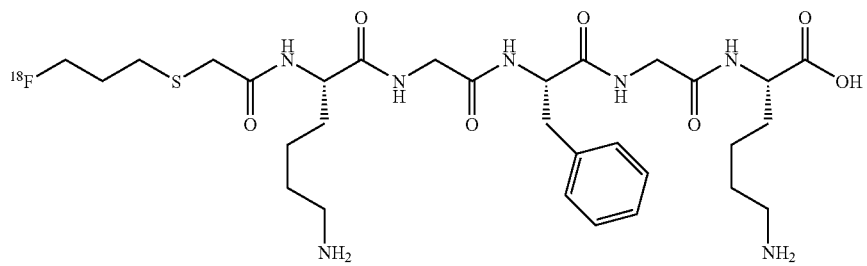

A solution of product from 5 a) in acetonitrile (0.5 ml, 1.1 mCi) was evaporated to dryness using a stream of nitrogen and heating at 100° C. A mixture of TFA (0.05 ml), triisopropylsilane (0.01 ml), and water (0.01 ml) was added followed by heating for 10 min at 80° C. After the vial was cooled to 0° C., ammonia (27% in water, 0.1 ml) and Cl—CH$_2$CO-Lys-Gly-Phe-Gly-Lys-OH (1 mg) in water (0.05 ml) were added. The mixture was stirred for 30 min at 80° C. Analysis by HPLC (gradient 2) revealed formation of desired product with a radiochemical purity of 93%.

Example 6

Preparation of (2-{2-[2-(2-[$^{18}$F]-Fluoro-ethoxy)-ethoxy]-ethoxy}-ethyl-trityl sulfide, Deprotection and Site-specific Conjugation to a Chloroacetyl Modified Peptide 6.a) Preparation of $^{18}$F synthon: 2-{2-[2-(2-[$^{18}$F]Fluoro-ethoxy)-ethoxy]-ethoxy}-mercaptotrityl-ethane

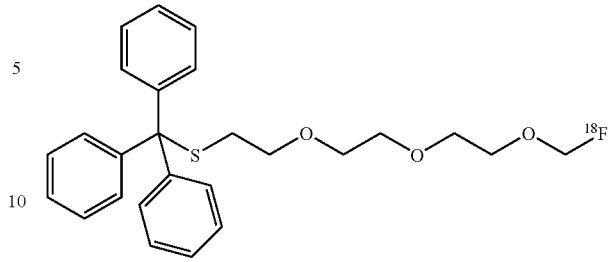

This preparation was carried out similarly as described in Example 5 a). After reacting the mesylate precursor prepared as described in Example 3 d) for 15 min in DMSO at 80° C. a radiochemical yield of 76% of product was obtained (HPLC). Extraction by Sep-Pak gave the desired product in a radiochemical purity of 97%.

6.b) Chemoselective ligation of to peptide Cl—CH$_2$CO-Lys-Gly-Phe-Gly-Lys-OH

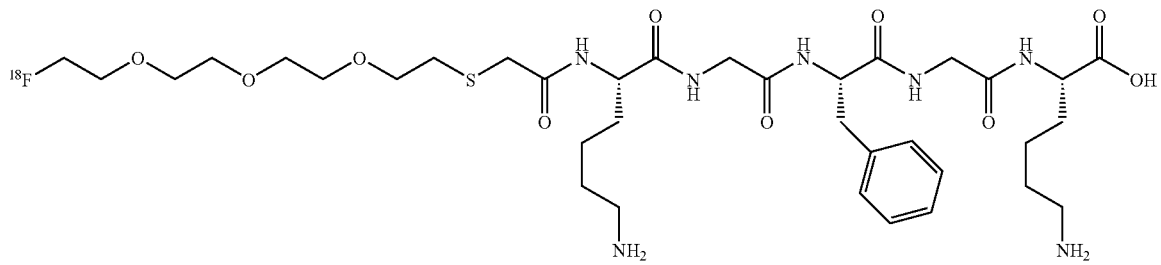

The deprotection and ligation reaction of $^{18}$F-synthon from Example 6 a) with peptide precursor Cl—CH$_2$CO-Lys-Gly-Phe-Gly-Lys-OH was carried out following the methods described in Example 5. HPLC analysis revealed formation of the desired product in a radiochemical purity of 41%.

Example 7

Synthesis of [Cys$^{2-6}$]cyclo[CH$_2$CO-Lys(4-{3-[2-(4-fluoromethyl-benzoylamino)-ethylsulfanyl]-2,5-dioxo-pyrrolidin-1-ylmethyl}-cyclohexane-1-carbonyl)-Cys$^2$-Arg-Gly-Asp-Cys$^6$-Phe-Cys]-NH$_2$

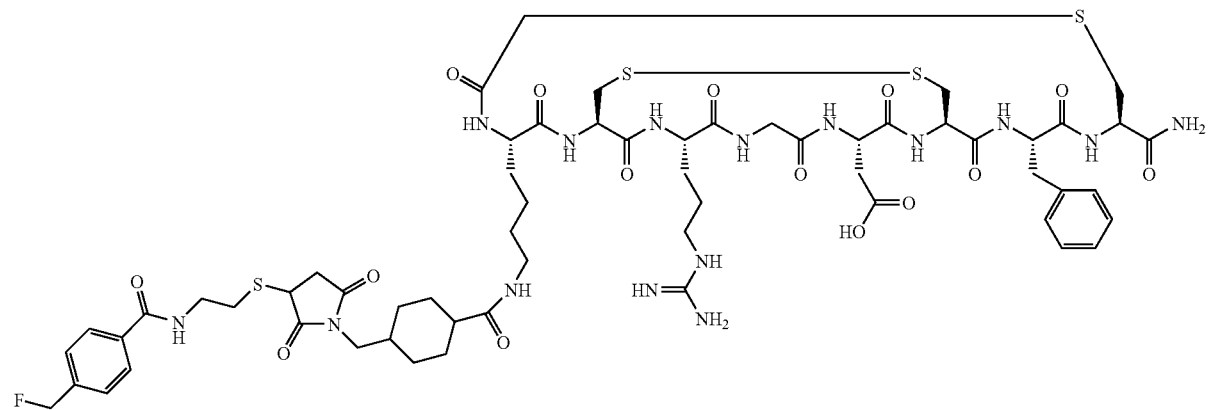

7 a) Synthesis of [Cys$^{2-6}$]cyclo[CH$_2$CO-Lys-Cys$^2$-Arg-Gly-Asp-Cys$^6$-Phe-Cys]-NH$_2$
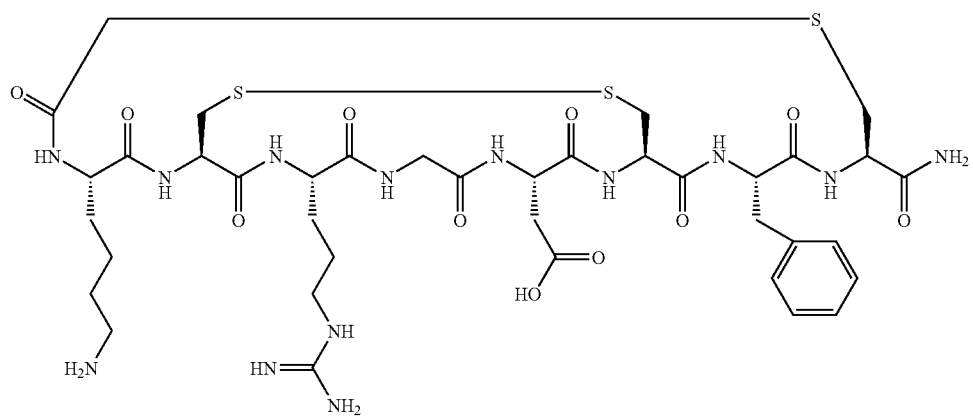
The title compound was synthesised as described in WO 03/006491.
7 b) Synthesis of [Cys$^{2-6}$]cyclo[CH$_2$CO-Lys(4-[N-maleimidomethyl]-cyclohexane-1-carbonyl)-Cys$^2$-Arg-Gly-Asp-Cys$^6$-Phe-Cys]-NH$_2$
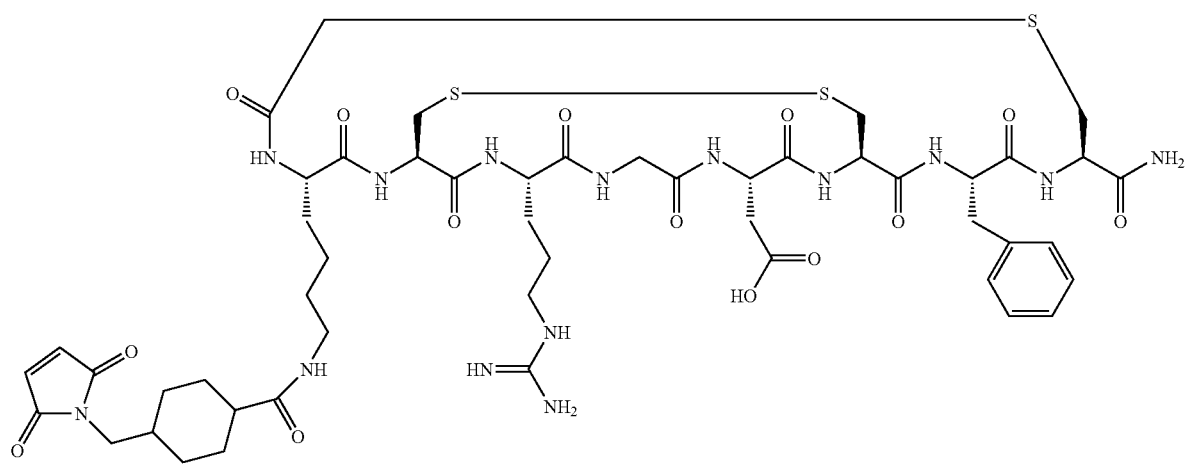

To 5 mg of the peptide from 4 a) above in DMF 1 mL was added 3 mg of sulfosuccinimidyl 4-[N-maleimidomethyl] cyclolhexane-1-carboxylate (Pierce) and 0.05 mL NMM. The reaction was left stirring at room temperature for 2 hours then diluted with 5 mL of water and charged onto a semi-preparative Luna C18 column. The product fraction was collected and freeze-dried yielding 1 mg of desired product. The structure was confirmed by MALDI-MS: Expected M+H+,1189; Found 1190.

7. c) Site-specific Conjugation to the Maleimide Modified Peptide

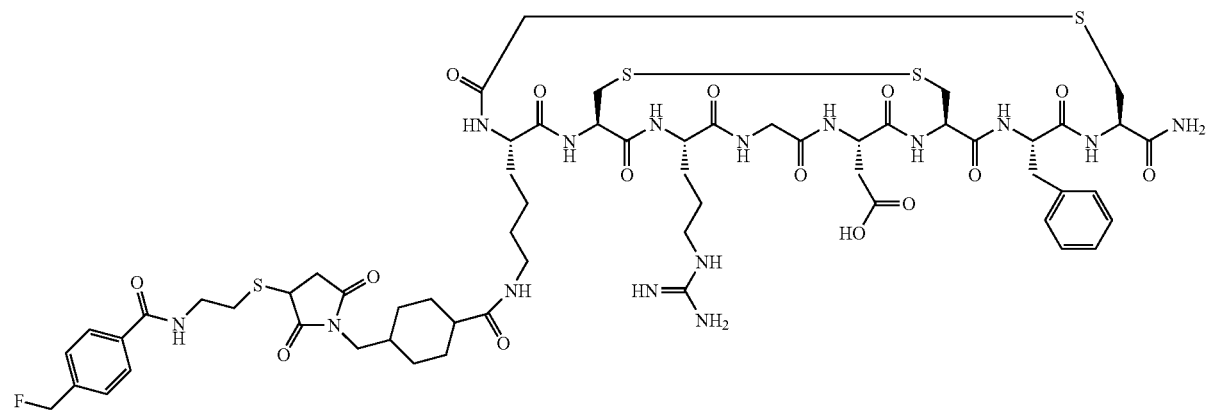

To 0.16 mg (0.34 μmol) of 4-fluoromethyl-N-[2-(tritylsulphanyl)ethyl]benzamide (from example 1 d above) was added 50 μl of TFA/TIS/H$_2$O (95:2.5:2.5) mixture. The flask was swirled gently for 5 minutes and then concentrated in vacuo. The residue was taken up in 50 μl water. To the mixture was added a solution of 0.4 mg (0.34 μmol) maleimide modified peptide in 50 μl water and pH adjusted to 6.5 with 0.001 M sodium hydroxide. After 50 minutes LC-MS analysis (column Phenomenex Luna 3 μm C18(2) 50×2.00 mm; solvents: A=water/0.1% HCOOH 20 and B=acetonitrile/0.1% HCOOH; gradient 0-50% B over 10 min; flow 0.3 ml/min, UV detection at 214 and 254 nm, ESI-MS) showed almost complete conversion of the maleimide modified peptide to a new product($t_R$ 7.6 min) giving m/z at 1400.7 corresponding to the M+H+ for the conjugate.

Example 8

Synthesis of [Cys$^{2-6}$]cyclo[CH$_2$CO-Lys(4-{3-[2-(4-[$^{18}$F]-fluoromethyl-benzoylamino)-ethylsulfanyl]-2,5-dioxo-pyrrolidin-1-ylmethyl}-cyclohexane-1-carbonyl)Cys$^2$-Arg-Gly-Asp-Cys$^6$-Phe-Cys]-NH$_2$ The title compound is prepared from the modified peptide of Example 7b by reaction with 4-[$^{18}$F]-fluoromethyl-N-[2-(tritylsulphanyl)ethyl]benzamide (Example 4) using methods analogous to those described in Example 7c.

It is apparent that many modifications and variations of the invention as hereinabove set forth may be made without departing from the spirit and scope thereof. The specific embodiments described are given by way of example only, and the invention is limited only by the terms of the appended claims.

The invention claimed is:

1. A method for radiofluorination comprising reaction of a compound of formula (I) or (Ia):

   (I)

-continued

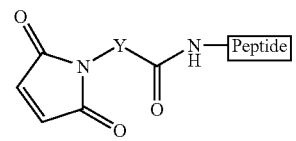   (Ia)

with a compound of formula (II):

$^{18}$F-(Linker)-SH   (II)

wherein:
X is a leaving group selected from chloro, bromo, and iodo, and is preferably chloro;
Y is a C$_{1-10}$ hydrocarbyl group optionally including 1 to 6 heteroatoms; and
the Linker in formula (II) is a C$_{1-30}$ hydrocarbyl group optionally further including 1 to 10 heteroatoms;
to give a compound of formula (III) or (IIIa) respectively:

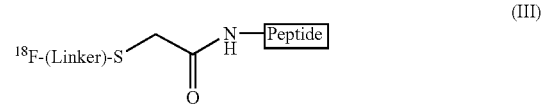   (III)

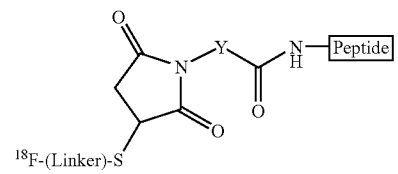   (IIIa)

wherein the Linker group is as defined in the compound of formula (II), Y is as defined in the compound of formula (Ia).

2. A method for radiofluorination comprising reaction of a compound of formula (I):

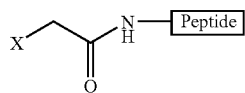
(I)

with a compound of formula (IV), (V), or (VI):

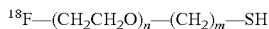
(IV)

(V)

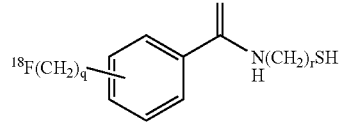
(VI)

wherein:

X is a leaving group selected from chloro, bromo, and iodo, and is preferably chloro;

n is an integer of 1 to 20;

m is an integer of 1 to 10;

p is an integer of 1 to 20;

q is an integer of 0 to 4;

r is an integer of 1 to 10;

to give a compound of formula (VII), (VII), or (IX) respectively:

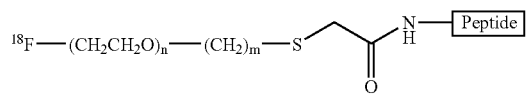
(VII)

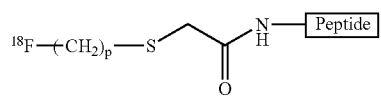
(VIII)

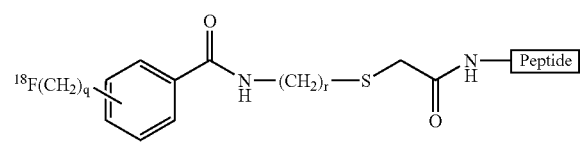
(IX)

wherein m, n, p, q, and r are as defined for the compound of formula (IV), (V), or (VI).

3. A method for radiofluorination comprising reaction of a compound of formula (Ia):

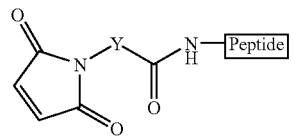
(Ia)

with a compound of formula (IV), (V), or (VI):

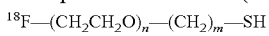
(IV)

(V)

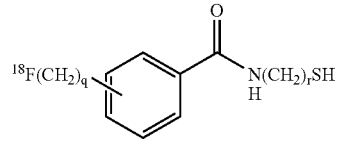
(VI)

wherein:

Y is a $C_{1-10}$ hydrocarbyl group optionally further including 1 to 6 heteroatoms;

n is an integer of 1 to 20;

m is an integer of 1 to 10;

p is an integer of 1 to 20;

q is an integer of 0 to 4;

r is an integer of 1 to 10;

to give a compound of formula (X), (XI), or (XII) respectively:

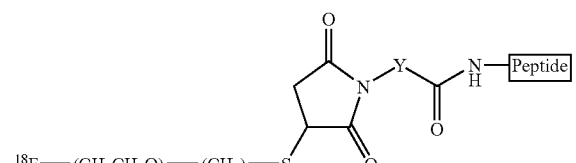
(X)

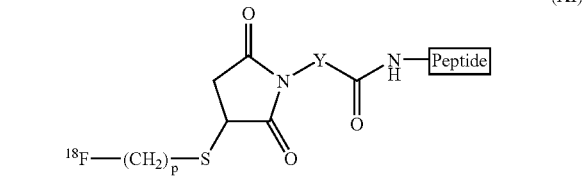
(XI)

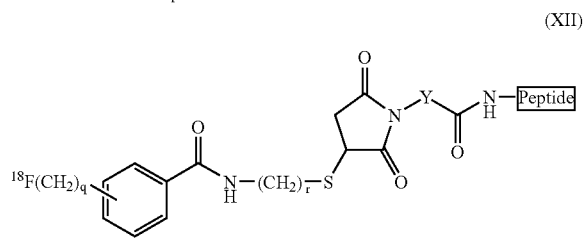
(XII)

wherein m, n, p, q, and r are as defined for the compound of formula (IV), (V), or (VI), and Y is as defined for the compound of formula (Ia).

* * * * *